United States Patent
Murai et al.

(10) Patent No.: US 9,409,119 B2
(45) Date of Patent: Aug. 9, 2016

(54) ACID GAS ABSORBENT, ACID GAS REMOVAL METHOD, AND ACID GAS REMOVAL DEVICE

(75) Inventors: Shinji Murai, Sagamihara (JP); Yukishige Maezawa, Hachioji (JP); Yasuhiro Kato, Kawasaki (JP); Takehiko Muramatsu, Yokohama (JP); Satoshi Saito, Yamato (JP); Hiroko Watando, Tokyo (JP); Naomi Shida, Tokyo (JP); Reiko Yoshimura, Kawasaki (JP); Takashi Kuboki, Tokyo (JP)

(73) Assignee: KABUSHIKI KAISHA TOSHIBA, Tokyo (JP)

( * ) Notice: Subject to any disclaimer, the term of this patent is extended or adjusted under 35 U.S.C. 154(b) by 384 days.

(21) Appl. No.: 13/332,018

(22) Filed: Dec. 20, 2011

(65) Prior Publication Data
US 2012/0161071 A1    Jun. 28, 2012

(30) Foreign Application Priority Data

Dec. 22, 2010  (JP) ................ P2010-286554
Nov. 11, 2011  (JP) ................ P2011-247775
Nov. 11, 2011  (JP) ................ P2011-247776

(51) Int. Cl.
*C09K 3/00*  (2006.01)
*B01D 53/14*  (2006.01)
*C07C 215/08*  (2006.01)

(52) U.S. Cl.
CPC ........ *B01D 53/1493* (2013.01); *B01D 53/1475* (2013.01); *C07C 215/08* (2013.01);
(Continued)

(58) Field of Classification Search
CPC ........... B01D 53/1493; B01D 53/1475; B01D 215/08; B01D 2252/20426; B01D 2252/20431; B01D 2252/20442; B01D 2252/20447; B01D 2252/504; B01D 2252/602; Y02C 10/06
USPC .......................................... 252/189, 190, 192
See application file for complete search history.

(56) References Cited

U.S. PATENT DOCUMENTS 4,101,633 A    7/1978 Sartori et al.
4,112,052 A    9/1978 Sartori et al.
(Continued)

FOREIGN PATENT DOCUMENTS

CA    2 576 454    10/2006
EP    0 647 462 A1    4/1995
(Continued)

OTHER PUBLICATIONS
STIC Search Report dated Jul. 25, 2014.*
(Continued)

*Primary Examiner* — Eisa Elhilo
(74) *Attorney, Agent, or Firm* — Finnegan, Henderson, Farabow, Garrett & Dunner, LLP

(57) ABSTRACT

An acid gas absorbent of which recovery amount of acid gas such as carbon dioxide is high, and an acid gas removal device and an acid gas removal method using the acid gas absorbent are provided. The acid gas absorbent of the embodiment comprising at least one type of tertiary amine compound represented by the following general formula (1).

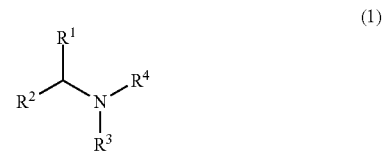

(1)

(In the above-stated formula (1), either one of the $R^1$, $R^2$ represents a substituted or non-substituted alkyl group of which carbon number is 2 to 5, and the other one represents a substituted or non-substituted alkyl group of which carbon number is 1 to 5. The $R^3$ represents a methyl group or an ethyl group, and the $R^4$ represents a hydroxyalkyl group. The $R^1$, $R^2$ may either be the same or different, and they may be coupled to form a cyclic structure.)

20 Claims, 1 Drawing Sheet

(52) U.S. Cl.
CPC ............... *B01D2252/20426* (2013.01); *B01D 2252/20431* (2013.01); *B01D 2252/20442* (2013.01); *B01D 2252/20447* (2013.01); *B01D 2252/20484* (2013.01); *B01D 2252/504* (2013.01); *B01D 2252/602* (2013.01); *Y02C 10/06* (2013.01); *Y02P 20/152* (2015.11)

(56) References Cited

U.S. PATENT DOCUMENTS

| | | | |
|---|---|---|---|
| 4,238,206 A | | 12/1980 | Hong |
| 4,508,692 A | | 4/1985 | Savage et al. |
| 5,209,914 A | | 5/1993 | Peytavy et al. |
| 5,618,506 A | * | 4/1997 | Suzuki et al. ............... 423/228 |
| 6,030,931 A | | 2/2000 | Vinski et al. |
| 6,500,397 B1 | | 12/2002 | Yoshida et al. |
| 8,147,593 B2 | | 4/2012 | Mimura et al. |
| 8,419,831 B2 | | 4/2013 | Shimizu et al. |
| 2009/0211447 A1 | | 8/2009 | Lichtfers et al. |
| 2010/0180764 A1 | | 7/2010 | Inoue et al. |

FOREIGN PATENT DOCUMENTS

| | | |
|---|---|---|
| EP | 2 168 658 A1 | 3/2010 |
| EP | 2 189 207 A1 | 5/2010 |
| EP | 2 354 191 A1 | 8/2011 |
| GB | 831091 | 3/1960 |
| GB | 1 238 696 | 7/1971 |
| GB | 1 463 516 | 2/1977 |
| JP | 58-124519 | 7/1983 |
| JP | 5-301023 | 11/1993 |
| JP | 8-257354 | 10/1996 |
| JP | 2871334 | 1/1999 |
| JP | 2008-238073 | 10/2008 |
| JP | 2008-307519 | 12/2008 |
| JP | 2009-6275 | 1/2009 |
| JP | 2009-213972 | 9/2009 |
| WO | WO 2006/107026 A1 | 10/2006 |
| WO | WO 2007/068695 A1 | 6/2007 |
| WO | WO 2009/001804 A1 | 12/2008 |
| WO | WO 2009/110586 A1 | 9/2009 |

OTHER PUBLICATIONS

English translation of the Japanese Patent No. JP 3529855 dated Aug. 1, 2014.*
RN 1153555-00-0 STN Registry (Jun. 7, 2009).*
RN 1022658-90-7 STN Registry (May 26, 2006).*
Partial European Search Report issued by the European Patent Office on May 14, 2012, for European Patent Application No. 11195018.4.
Rolker et al., Abtrennung von Kohlen-dioxid aus Rauchgasen mittels Absorption, Chemie Ingenieur Technik (Jan. 1, 2006), pp. 416-424.
Office Action issued by the Canadian Intellectual Property Office on Oct. 29, 2013, for Canadian Patent Application No. 2,762,180.
Examination Report issued by the European Patent Office on Jan. 22, 2014, for European Patent Application No. 11 195 018.4.
Extended European Search Report issued by the European Patent Office on Oct. 26, 2012, for European Patent Application No. 11195018.4.
Bennett, "Corrosion Inhibitors as Preservatives for Metalworking Fluids—Ethanolamines," Journal of the American Society of Lubrication Engineers, 35:137-144 (Mar. 1, 1979).
Third Office Action issued by the State Intellectual Property Office of the People's Republic of China on May 19, 2015, for Chinese Patent Application No. 201110433500.0, and English-language translation thereof.
RN 1153555-00-0, STN Registry, Jun. 7, 2009.
RN 1022658-90-7, STN Registry, May 26, 2008.

* cited by examiner

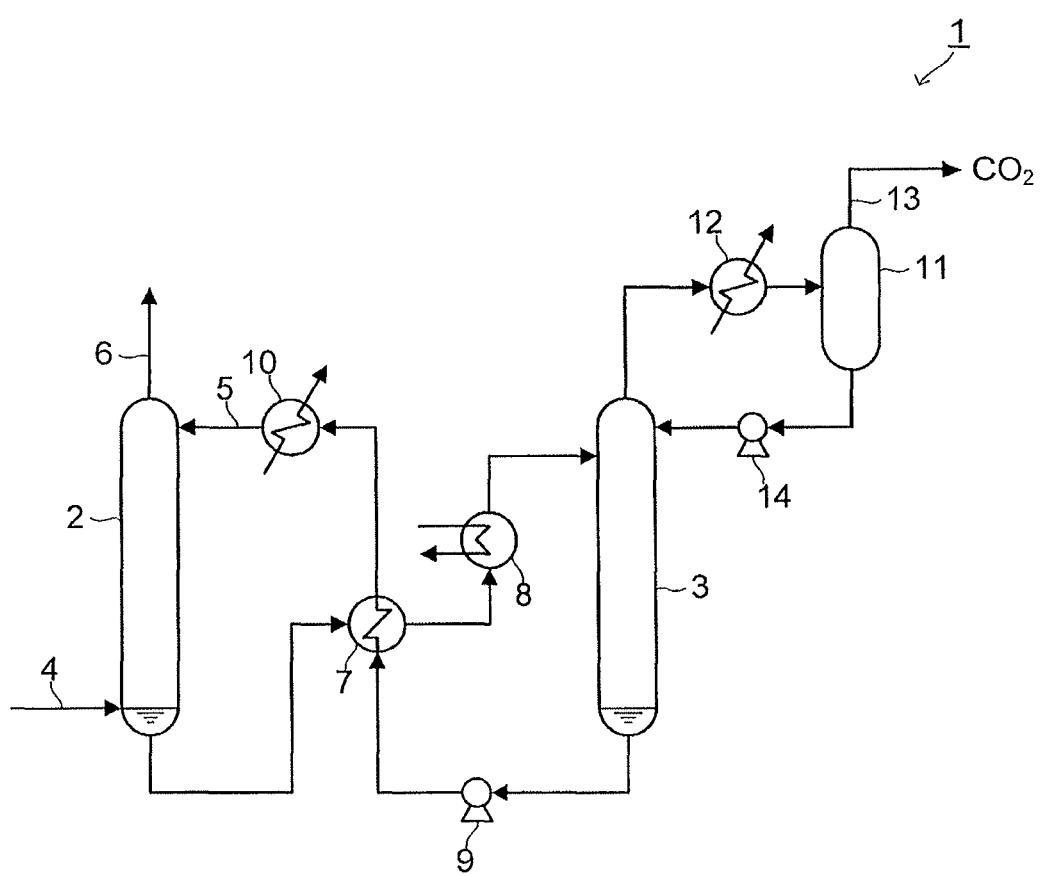

ACID GAS ABSORBENT, ACID GAS REMOVAL METHOD, AND ACID GAS REMOVAL DEVICE

CROSS-REFERENCE TO RELATED APPLICATIONS

This application is based upon and claims the benefit of priority from the prior Japanese Patent Application No. 2010-286554, filed on Dec. 22, 2010; Japanese Patent Application No. 2011-247775, filed on Nov. 11, 2011; and Japanese Patent Application No. 2011-247776, filed on Nov. 11, 2011; the entire contents of which are incorporated herein by reference.

FIELD

Embodiments described herein relate generally to an acid gas absorbent, an acid gas removal device, and an acid gas removal method using the acid gas absorbent.

BACKGROUND

In recent years, a greenhouse effect resulting from an increase of a carbon dioxide ($CO_2$) concentration is pointed out as a cause of global warming phenomena, and there is an urgent need to device an international countermeasure to protect environment in a global scale. Industrial activities have a large responsibility as a generation source of $CO_2$, and there is a trend to suppress discharge of $CO_2$.

As technologies to suppress the increase of an acid gas concentration starting with $CO_2$, there are a development of energy saving products, a separation and recovery technology of discharged acid gas, technologies to use the acid gas as a resource and to isolate and store the acid gas, a switching to alternate energies such as natural energy, atomic energy, and so on which do not discharge the acid gas, and so on.

As a separation technology of the acid gas studied up to now, there are an absorption process, a suction process, a membrane separation process, a cryogenic process, and so on. Among them, the absorption process is suitable for processing a large amount of gas, and an application for a factory, a power station is considered.

Accordingly, a method in which exhaust gas generated when fossil fuel (coal, coal oil, natural gas, and so on) is burned is brought into contact with a chemical absorbent to remove and recover $CO_2$ in exhaust combustion gas, and further a method storing the recovered $CO_2$ are performed throughout the world in a facility such as a thermal power station using the fossil fuel. Besides, acid gas such as hydrogen sulfide ($H_2S$) in addition to $CO_2$ are removed by using the chemical absorbent is proposed.

In general, alkanolamines represented by monoethanolamine (MEA) have been developed from 1930 years as the chemical absorbent used in the absorption process, and it is still used at present. This method is economical and it is easy to increase the removal device in size.

As existing and widely used alkanolamines, there are monoethanolamine, 2-amino-2-methylpropanolamine, methylaminoethanol, ethylaminoethanol, propylaminoethanol, diethanolamine, methyldiethanolamine, dimethylethanolamine, diethylethanolamine, triethanolamine, dimethylamino-1-methylethanol, and so on.

In particular, primary monoethanolamine and so on are widely used because their reaction rates are fast. However, there are problems in which this compound has corrosiveness, is easy to be deteriorated, and requires high energy for regeneration. On the other hand, tertiary methyldiethanolamine has low corrosiveness, and requires low energy for regeneration, but has a defect that an absorption speed is low. Accordingly, a development of a new absorbent improving these points is required.

In recent years, a study for alkanolamine particularly having structural steric hindrance is vigorously tried as the absorbent of acid gas among amino based compounds. The alkanolamine having the steric hindrance has merits in which selectivity of acid gas is very high, and the energy required for regeneration is small.

The reaction speed of the amine based compound having the steric hindrance depends on a degree of reaction hindrance determined by a steric structure thereof. The reaction speed of the amine based compound having the steric hindrance is lower than the secondary amine, for example, such as methylethanolamine, diethanolamine, but higher than the tertiary amine. Besides, 2-amino-2-methylpropanol, 2-piperidineethanol, and so on are known as the alkanolamine to be compounded in the absorbent.

On the other hand, a method using a cyclic amine as the absorbent as the amine based compound having a structure different from the alkanolamines is also known.

BRIEF DESCRIPTION OF THE DRAWINGS

FIG. 1 is a schematic diagram of an acid gas removal device according to an embodiment.

DETAILED DESCRIPTION

However, these technologies are still insufficient relating to absorption capacities of acid gas such as an absorption amount of acid gas, an absorption speed of acid gas, and further improvement of gas absorption capacities is required. Besides, the one of which absorption amount of acid gas is higher is required to further enhance recovery efficiency of acid gas.

A problem to be solved by the present embodiments is to provide an acid gas absorbent of which absorption amount of acid gas such as carbon dioxide is large and a recovery amount of acid gas is high, an acid gas removal device and an acid gas removal method using the acid gas absorbent.

An acid gas absorbent according to a first embodiment comprising at least one type of tertiary amine compound represented by the following general formula (1).

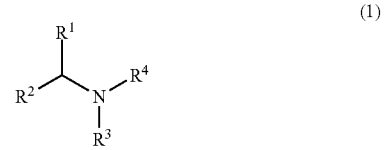

(1)

(In the above-stated formula (1), either one of the $R^1$, $R^2$ represents a substituted or non-substituted alkyl group of which carbon number is 2 to 5, and the other one represents a substituted or non-substituted alkyl group of which carbon number is 1 to 5. The $R^3$ represents a methyl group or an ethyl group, and the $R^4$ represents a hydroxyalkyl group. The $R^1$, $R^2$ may either be the same or different, and they may be coupled to form a cyclic structure.)

Besides, the acid gas absorbent according to a second embodiment comprising at least one type of secondary amine compound represented by the following general formula (4).

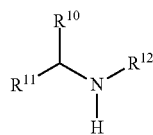

(4)

(In the above-stated formula (4), either one of the $R^{10}$, $R^{11}$ represents a substituted or non-substituted alkyl group of which carbon number is 2 to 5, and the other one represents a substituted or non-substituted alkyl group of which carbon number is 1 to 5. The $R^{12}$ represents the hydroxyalkyl group. The $R^{10}$, $R^{11}$ may either be the same or different, and they may be coupled to form the cyclic structure. When the $R^{10}$, $R^{11}$ form the cyclic structure, the $R^{10}$, $R^{11}$ each represent the substituted or non-substituted alkyl group of which carbon number is 1 to 5.)

An acid gas removal method according to the embodiment is to remove the acid gas from gas containing the acid gas by bringing the gas containing the acid gas into contact with the acid gas absorbent according to the embodiment.

An acid gas removal device according to the embodiment comprising: an absorption tower bringing the gas containing the acid gas into contact with the acid gas absorbent according to the embodiment to remove the acid gas from the gas; and a regeneration tower removing the acid gas from the acid gas absorbent absorbing the acid gas and regenerating the acid gas absorbent to be reused at the absorption tower.

Hereinafter, embodiments are described in detail. An acid gas absorbent according to the first embodiment is characterized in that it comprises at least one type of tertiary amine compound represented by the following general formula (1).

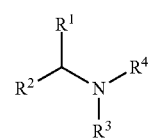

(1)

(In the above-stated formula (1), either one of the $R^1$, $R^2$ represents a substituted or non-substituted alkyl group of which carbon number is 2 to 5, and the other one represents a substituted or non-substituted alkyl group of which carbon number is 1 to 5. The $R^3$ represents a methyl group or an ethyl group, and the $R^4$ represents a hydroxyalkyl group. The $R^1$, $R^2$ may either be the same or different, and they may be coupled to form a cyclic structure.)

Conventionally, it is known that a steric hindrance held by the amine compound has a large influence on a product at a carbon dioxide absorption time, and plays an advantageous role on a generation of bicarbonate ion showing low heat of reaction. For example, it is reported that N-(isopropyl)-N-methylaminoethanol having a branch structure shows low heat of reaction for an absorption reaction of carbon dioxide. The present inventors examined based on the above-stated information to obtain a larger effect of the steric hindrance, and as a result, they found that it is possible to obtain further lower heat of reaction by using the compound represented in the above-stated general formula (1) (for example, N-(sec-butyl)-N-methylaminoethanol) than the conventional amino compound having the branch structure.

Namely, in the tertiary amine compound of the general formula (1), the methyl group or the ethyl group ($R^3$) and the hydroxyalkyl group ($R^4$) are each coupled to a nitrogen atom. The tertiary amine compound of the general formula (1) further has the branch structure in which two alkyl groups ($R^1$, $R^2$) are coupled to one carbon atom which is coupled to the nitrogen atom.

As stated above, the tertiary amine compound of the general formula (1) in which the branched alkyl groups are directly coupled to the nitrogen atom has a structure of which steric hindrance is large. Accordingly, it is conceivable that the bicarbonate ion is generated and the heat of reaction is reduced in a reaction between the tertiary amine compound of the general formula (1) and carbon dioxide ($CO_2$).

The tertiary amine compound represented by the general formula (1) (hereinafter, it is referred to as the tertiary amine compound (1)) is dissolved in a solvent, for example, such as water, and thereby, an acid gas absorbent of which absorption capacity for the acid gas is high can be obtained. In the following embodiment, a case when the acid gas is carbon oxide is described as an example, but the acid gas absorbent according to the embodiment is able to obtain similar effect as for the other acid gas such as hydrogen sulfide.

The $R^1$, $R^2$ are groups coupling to the carbon atom which is coupled to the nitrogen atom. Either one of the $R^1$, $R^2$ is the substituted or non-substituted alkyl group of which carbon number is 2 to 5, and the other one is the substituted or non-substituted alkyl group of which carbon number is 1 to 5. The $R^1$, $R^2$ may either be the same or different. For example, branched or linear hydrocarbon groups such as the methyl group, the ethyl group, a propyl group, an isopropyl group, a butyl group, an s-butyl group can be used as the substituted or non-substituted alkyl group of which carbon number is 1 to 5, and these hydrocarbon groups may contain a hetero atom such as Si, O, N, S. It is more preferable to use the methyl group or the ethyl group as the substituted or non-substituted alkyl group of which carbon number is 1 to 5.

For example, branched or linear hydrocarbon groups such as the ethyl group, the propyl group, the isopropyl group, the butyl group, the s-butyl group can be used as the substituted or non-substituted alkyl group of which carbon number is 2 to 5, and these hydrocarbon groups may contain the hetero atom such as Si, O, N, S. It is more preferable to use the ethyl group as the substituted or non-substituted alkyl group of which carbon number is 2 to 5.

The tertiary amine compound (1) in which at least either one of the $R^1$, $R^2$ is the alkyl group of which carbon number is 2 or more has a small heat of reaction in a reaction with the acid gas, and has an excellent reactivity for the acid gas. Besides, the tertiary amine compound (1) in which at least either one of the $R^1$, $R^2$ is the alkyl group of which carbon number is 2 or more has a higher boiling point and volatile from absorbing liquid is difficult to occur compared to the tertiary amine compound in which both of the $R^1$, $R^2$ are the methyl groups.

The $R^1$, $R^2$ may form the cyclic structure in which the substituted alkyl group or the non-substituted alkyl group of which carbon number is 2 to 5 and the substituted alkyl group or the non-substituted alkyl group of which carbon number is 1 to 5 are coupled. A cyclopropyl group, a cyclobutyl group, a cyclopentyl group, a cyclohexyl group, a cycloheptyl group, a cyclooctyl group, a cyclononyl group can be cited as the cyclic structure.

The volatile of the tertiary amine compound of the formula (1) is suppressed by the cyclic structure formed by the $R^1$, $R^2$. Accordingly, it is possible to make an acid gas absorbent in which an amount of the amine component discharged into the atmosphere is reduced during the exhaust gas is processed. Besides, the heat of reaction of the tertiary amine compound of the formula (1) at the reaction time with the acid gas is reduced by the cyclic structure formed the $R^1$, $R^2$. The cyclopentyl group and the cyclohexyl group are more preferable among the above-stated cyclic structures from a point of view of solubility.

The $R^3$ is the methyl group or the ethyl group. The $R^3$ coupled to the nitrogen atom is set to be the methyl group or the ethyl group, and thereby, it is possible to reduce the heat of reaction of the tertiary amine compound (1) with the acid gas, and to improve the reactivity of the acid gas absorbent with carbon dioxide. The $R^3$ is more preferable to be the methyl group.

The $R^4$ is the hydroxyalkyl group. It is preferable to be the hydroxyalkyl group of which carbon number is 2 to 4 from a point of view of improving the reactivity with carbon dioxide. The hydroxyalkyl group of the $R^4$ is more preferable to be a 2-hydroxyethyl group.

For example, N-(2-butyl)-N-methylaminoethanol, N-(2-pentyl)-N-methylaminoethanol, N-(2-hexyl)-N-methylaminoethanol, N-(3-pentyl)-N-methylaminoethanol, N-(3-hexyl)-N-methylaminoethanol, N-(3-heptyl)-N-methylaminoethanol, N-(4-heptyl)-N-methylaminoethanol, N-(4-octyl)-N-methylaminoethanol, N-(5-nonyl)-N-methylaminoethanol, N-(2-butyl)-N-ethylaminoethanol, N-(2-pentyl)-N-ethylaminoethanol, N-(2-hexyl)-N-ethylaminoethanol, N-(3-pentyl)-N-ethylaminoethanol, N-(3-hexyl)-N-ethylaminoethanol, N-(3-heptyl)-N-ethylaminoethanol, N-(4-heptyl)-N-ethylaminoethanol, N-(4-octyl)-N-ethylaminoethanol, N-(5-nonyl)-N-ethylaminoethanol, N-(2-butyl)-N-methylaminopropanol, N-(2-pentyl)-N-methylaminopropanol, N-(2-hexyl)-N-methylaminopropanol, N-(3-pentyl)-N-methylaminopropanol, N-(3-hexyl)-N-methylaminopropanol, N-(3-heptyl)-N-methylaminopropanol, N-(4-heptyl)-N-methylaminopropanol, N-(4-octyl)-N-methylaminopropanol, N-(5-nonyl)-N-methylaminopropanol, N-(2-butyl)-N-ethylaminopropanol, N-(2-pentyl)-N-ethylaminopropanol, N-(2-hexyl)-N-ethylaminopropanol, N-(3-pentyl)-N-ethylaminopropanol, N-(3-hexyl)-N-ethylaminopropanol, N-(3-heptyl)-N-ethylaminopropanol, N-(4-heptyl)-N-ethylaminopropanol, N-(4-octyl)-N-ethylaminopropanol, N-(5-nonyl)-N-ethylaminopropanol, N-(2-butyl)-N-methylaminobutanol, N-(2-pentyl)-N-methylaminobutanol, N-(2-hexyl)-N-methylaminobutanol, N-(3-pentyl)-N-methylaminobutanol, N-(3-hexyl)-N-methylaminobutanol, N-(3-heptyl)-N-methylaminobutanol, N-(4-heptyl)-N-methylaminobutanol, N-(4-octyl)-N-methylaminobutanol, N-(5-nonyl)-N-methylaminobutanol, N-(2-butyl)-N-ethylaminobutanol, N-(2-pentyl)-N-ethylaminobutanol, N-(2-hexyl)-N-ethylaminobutanol, N-(3-pentyl)-N-ethylaminobutanol, N-(3-hexyl)-N-ethylaminobutanol, N-(3-heptyl)-N-ethylaminobutanol, N-(4-heptyl)-N-ethylaminobutanol, N-(4-octyl)-N-ethylaminobutanol, N-(5-nonyl)-N-ethylaminobutanol can be cited as the tertiary amine compound (1) in which the branched alkyl group is coupled to the nitrogen atom.

As the tertiary amine compound (1) in which the $R^1$, $R^2$ form the cyclic structure, N-cyclopropyl-N-methylaminoethanol, N-cyclobutyl-N-methylaminoethanol, N-cyclopentyl-N-methylaminoethanol, N-cyclohexyl-N-methylaminoethanol, N-cycloheptyl-N-methylaminoethanol, N-cyclooctyl-N-methylaminoethanol, and so on can be cited.

Note that one type of compound selected from the above-stated group can be used as the tertiary amine compound (1), and the one in which two or more type of compounds selected from the above-stated group are mixed can be used as the tertiary amine compound (1).

It is preferable that a content of the tertiary amine compound (1) contained in the acid gas absorbent is 10 mass % to 55 mass %. In general, the absorption amount, a desorption amount of carbon dioxide per a unit capacity are larger and an absorption speed, a desorption speed of carbon dioxide are faster as a concentration of the amine component is higher, and therefore, it is preferable in an energy consumption side, a size of a plant facility, and a process efficiency side. However, it becomes impossible for the water contained in the absorbing liquid to fully exhibit a function as an activator relative to the absorption of carbon dioxide when the concentration of the amine component in the absorbing liquid is too high. Besides, defects such as an increase of viscosity of the absorbing liquid become unable to disregard when the concentration of the amine component in the absorbing liquid is too high. When the content of the tertiary amine compound (1) is 55 mass % or less, phenomena such as the increase of the viscosity of the absorbing liquid, the deterioration of the function of water as the activator are not recognized. Besides, the content of the tertiary amine compound (1) is set to be 10 mass % or more, and thereby, it is possible to obtain the enough absorption amount, absorption speed of carbon dioxide, and to obtain excellent process efficiency.

Not only the absorption amount of carbon dioxide and the absorption speed of carbon dioxide are high but also the desorption amount of carbon dioxide and the desorption speed of carbon dioxide are high when the acid gas absorbent of which content of the tertiary amine compound (1) is within a range of 10 mass % to 55 mass is used for recovery of carbon dioxide. Accordingly, it is advantageous in a point that the recovery of carbon dioxide can be performed effectively. The content of the tertiary amine compound (1) is more preferable to be 20 mass % to 50 mass %.

It is preferable that the tertiary amine compound (1) is used while being mixed with a reaction accelerator composed of alkanolamines and/or a hetero cyclic amine compound represented by the following general formula (2) (hereinafter referred to as the hetero cyclic amine compound (2)).

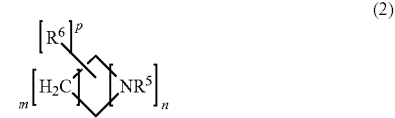

(2)

In the formula (2), the $R^5$ represents a hydrogen atom or a substituted or non-substituted alkyl group of which carbon number is 1 to 4. The $R^6$ represents the substituted or non-substituted alkyl group of which carbon number is 1 to 4 coupled to the carbon atom. The "n" represents an integer number of 1 to 3, the "m" represents an integer number of 1 to 4, and the "p" represents an integer number of "0" (zero) to 12. When the "n" is 2 to 3, the nitrogen atoms are not directly coupled with each other.

In the present embodiment, it is possible to mix, for example, the tertiary amine compound (1) and the reaction accelerator composed of the alkanolamines and/or the hetero cyclic amine compound (2). In addition, it is possible to use the one in which the mixture of the tertiary amine compound (1) and the alkanolamines and/or the hetero cyclic amine compound (2) is made into, for example, a water solution as the acid gas absorbent. The tertiary amine compound (1) is used while being mixed with the alkanolamines and/or the hetero cyclic amine compound (2), and thereby, it is possible to further improve the absorption amount of carbon dioxide per unit mol of the tertiary amine compound (1), the absorption amount of carbon dioxide per unit volume of the acid gas absorbent and the absorption speed of carbon dioxide. Besides, the tertiary amine compound (1) is used while being mixed with the alkanolamines and/or the hetero cyclic amine compound (2), and thereby, an energy separating the acid gas after the absorption of carbon dioxide (acid gas desorption energy) is lowered, and it becomes possible to reduce the energy when the acid gas absorbent is regenerated.

For example, monoethanolamine, 2-amino-2-methylpropanolamine, 2-amino-2-methyl-1,3-dipropanolamine, methylaminoethanol, ethylaminoethanol, propylaminoethanol, diethanolamine, bis(2-hydroxy-1-methylethyl)amine, methyldiethanolamine, dimethylethanolamine, diethylethanolamine, triethanolamine, dimethylamino-1-methylethanol, 2-methylaminoethanol, 2-ethylaminoethanol, 2-propylaminoethanol, n-butylaminoethanol, 2-(isopropylamino)ethanol, 3-ethylaminopropanol, triethanolamine, diethanolamine, and so on can be cited as alkanolamine.

Among them, it is preferable to be at least one type selected from a group consisting of 2-(isopropylamino)ethanol, 2-(ethylamino)ethanol, and 2-amino-2-methyl-1-propanol as the alkanolamines from a point of view of improving the reactivity between the tertiary amine and the acid gas.

As the hetero cyclic amine compound (2), azetidine, 1-methylazetidine, 1-ethylazetidine, 2-methylazetidine, 2-azetidinemethanol, 2-(2-aminoethyl)azetidine, pyrrolidine, 1-methylpyrrolidine, 2-methylpyrrolidine, 2-butylpyrrolidine, 2-pyrrolidinemethanol, 2-(2-aminoethyl)pyrrolidine, piperidine, 1-methylpiperidine, 2-ethylpiperidine, 3-propylpiperidine, 4-ethylpiperidine, 2-piperidinemethanol, 3-piperidineethanol, 2-(2-aminoethyl)pyrrolidine, hexahydro-1H-azepine, hexamethylenetetramine, piperazine, piperazine derivatives, and so on can be cited.

Among them, the piperazine derivative is particularly desirable from points of view of improvements of the absorption amount and the absorption speed of carbon dioxide of the acid gas absorbent. The piperazine derivative is the secondary amine compound, and in general, the nitrogen atom of the secondary amino group is coupled to carbon dioxide to form carbamate ion, and thereby, it contributes to the improvement of the absorption speed at an initial stage of the reaction. Further, the nitrogen atom of the secondary amino group has a role of converting carbon dioxide coupled thereto into bicarbonate ($HCO_3^-$), and contributes to the improvement of speed at a half stage after the reaction.

It is more preferable that at least one type from among 2-methylpiperazine, 2,5-dimethylpiperazine, 2,6-dimethylpiperazine is the piperazine derivative.

It is preferable that the content of the reaction accelerator (the alkanolamines and/or the hetero cyclic amine compound (2)) contained in the acid gas absorbent is 1 mass % to 20 mass %. There is a possibility that the effect improving the absorption speed of carbon dioxide cannot be fully obtained when the content of the reaction accelerator contained in the acid gas absorbent is less than 1 mass %. There is a possibility that the reactivity conversely deteriorates because the viscosity of the absorbent becomes excessively high when the content of the reaction accelerator contained in the acid gas absorbent exceeds 20 mass %. The content of the reaction accelerator (the alkanolamines and/or the hetero cyclic amine compound (2)) is more preferable to be 5 mass % to 15 mass %.

Besides, an acid gas absorbent according to a second embodiment is characterized in that it comprises at least one kind of secondary amine compound represented by the following general formula (4).

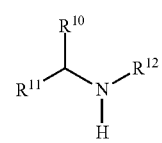

(4)

(In the above-stated formula (4), either one of the $R^{10}$, $R^{11}$ represents a substituted or non-substituted alkyl group of which carbon number is 2 to 5, and the other one represents a substituted or non-substituted alkyl group of which carbon number is 1 to 5. The $R^{12}$ represents a hydroxyalkyl group. The $R^{10}$, $R^{11}$ may either be the same or different, and they may be coupled to form the cyclic structure. When the $R^{10}$, $R^{11}$ form the cyclic structure, the $R^{10}$, $R^{11}$ each represent the substituted or non-substituted alkyl group of which carbon number is 1 to 5.)

The secondary amine compound of the general formula (4) has a branch structure in which two alkyl groups ($R^{10}$, $R^{11}$) are coupled to one carbon atom which is coupled to a nitrogen atom.

As stated above, the secondary amine compound of the general formula (4) in which the branched alkyl group is directly coupled to the nitrogen atom has a structure of which steric hindrance is large. Accordingly, it has high reactivity for the acid gas such as carbon dioxide ($CO_2$) and the high acid gas absorption amount can be obtained.

The secondary amine compounds represented by the general formula (4) (hereinafter, referred to as the secondary amine compound (4)) is dissolved into a solvent, for example, such as water, and thereby, the acid gas absorbent of which absorption capacity of the acid gas is high can be obtained.

The $R^{10}$, $R^{11}$ are groups coupled to the carbon atom which is coupled to the nitrogen atom in the formula (4). Either one of the $R^{10}$, $R^{11}$ represents the substituted or non-substituted alkyl group of which carbon number is 2 to 5, and the other one represents the substituted or non-substituted alkyl group of which carbon number is 1 to 5. The $R^{10}$, $R^{11}$ may either be the same or different. For example, branched or linear hydrocarbon groups such as the methyl group, the ethyl group, the propyl group, the isopropyl group, the butyl group, the s-butyl group can be used as the substituted or non-substituted alkyl group of which carbon number is 1 to 5, and these hydrocarbon groups may contain the hetero atom such as Si, O, N, S. It is more preferable to use the methyl group or the ethyl group as the substituted or non-substituted alkyl group of which carbon number is 1 to 5.

It is possible to use the branched or linear hydrocarbon group such as, for example, the ethyl group, the propyl group, the isopropyl group, the butyl group, the s-butyl group as the substituted or non-substituted alkyl group of which carbon number is 2 to 5, and these hydrocarbon groups may contain the hetero atom such as Si, O, N, S. It is more preferable to use the ethyl group as the substituted or non-substituted alkyl group of which carbon number is 2 to 5.

The secondary amine compound (4) in which at least either one of the $R^{10}$, $R^{11}$ is the alkyl group of which carbon number is 2 or more has small heat of reaction in the reaction with the acid gas and has excellent reactivity for the acid gas. Besides, the secondary amine compound (4) in which either one of the $R^{10}$, $R^{11}$ is the alkyl group of which carbon number is 2 or more has the higher boiling point and the volatile from the absorbing liquid is difficult to occur compared to the secondary amine compound in which both of the $R^{10}$, $R^{11}$ are the methyl groups.

The $R^{10}$, $R^{11}$ may be coupled to form the cyclic structure. When the $R^{10}$, $R^{11}$ form the cyclic structure, the $R^{10}$, $R^{11}$ each represent the substituted or non-substituted alkyl group of which carbon number is 1 to 5. The cyclopropyl group, the cyclobutyl group, the cyclopentyl group, the cyclohexyl group, the cycloheptyl group, the cyclooctyl group, the cyclononyl group can be cited as the cyclic structure.

The volatile of the secondary amine compound (4) is suppressed by the cyclic structure formed by the $R^{10}$, $R^{11}$. Accordingly, it is possible to make the acid gas absorbent in which an amount of the amine component discharged in the atmosphere is reduced during the exhaust gas is processed. Besides, the heat of reaction of the secondary amine compound of the formula (4) at the reaction time with the acid gas is reduced by the cyclic structure formed by the $R^{10}$, $R^{11}$. The cyclopentyl group and the cyclohexyl group are more preferable among the above-stated cyclic structures from a point of view of solubility.

The $R^{12}$ is the hydroxyalkyl group. It is preferable to be a hydroxyalkyl group of which carbon number is 2 to 4 from a point of view of improving the reactivity with carbon dioxide. The hydroxyalkyl group of the $R^{12}$ is more preferable to be the 2-hydroxyethyl group.

The following compounds can be cited as the secondary amine compound (4) in which the branched alkyl group is coupled to the nitrogen atom. Namely, 2-(2-butylamino)ethanol, 2-(2-pentylamino)ethanol, 2-(2-hexylamino)ethanol, 2-(3-pentylamino)ethanol, 2-(3-hexylamino)ethanol, 2-(3-heptylamino)ethanol, 2-(4-heptylamino)ethanol, 2-(4-octylamino)ethanol, 2-(5-nonylamino)ethanol, 3-(2-butylamino) propanol, 3-(2-pentylamino)propanol, 3-(2-hexylamino) propanol, 3-(3-pentylamino)propanol, 3-(3-hexylamino) propanol, 3-(3-heptylamino)propanol, 3-(4-heptylamino) propanol, 3-(4-octylamino)propanol, 3-(5-nonylamino) propanol, 4-(2-butylamino)butanol, 4-(2-pentylamino) butanol, 4-(2-hexylamino)butanol, 4-(3-pentylamino) butanol, 4-(3-hexylamino)butanol, 4-(3-heptylamino) butanol, 4-(4-heptylamino)butanol, 4-(4-octylamino) butanol, 4-(5-nonylamino)butanol, 2-(cyclopropylamino) ethanol, 2-(cyclobutylamino)ethanol, 2-(cyclopentylamino) ethanol, 2-(cyclohexylamino)ethanol, 2-(cycloheptylamino) ethanol, 2-(cyclooctylamino)ethanol, 3-(cyclopropylamino) propanol, 3-(cyclobutylamino)propanol, 3-(cyclopentylamino)propanol, 3-(cyclohexylamino)propanol, 3-(cycloheptylamino)propanol, 3-(cyclooctylamino) propanol, 4-(cyclopropylamino)propanol, 4-(cyclobutylamino)butanol, 4-(chiclopentylamino)butanol, 4-(cyclohexylamino)butanol, 4-(cycloheptylamino)butanol, 4-(cyclooctylamino)butanol, and so on can be cited as the secondary amine compound (4). Note that the one in which one type of compound or two types or more compounds selected from the above-stated group are mixed can be used as the secondary amine compound (4).

The secondary amine compound (secondary aminoalcohols) having the high boiling point is preferable as the secondary amine compound (4). The acid gas absorbent absorbing $CO_2$ is heated at a high-temperature range of approximately 120° C. to be regenerated. Accordingly, it is preferable to use the high-boiling point secondary amine compound as the secondary amine compound (4) which is difficult to be discharged from the regeneration tower when it is heated. It is therefore preferable to use the alkyl group as the secondary amine compound (4) having many carbon atoms. In particular, the secondary amine compound having the cyclic structure is preferable.

Note that it is possible to use one type of compound selected from the above-stated group as the secondary amine compound (4), or to use the one in which two or more types of compounds selected from the above-stated group are mixed.

It is preferable that a content of the secondary amine compound (4) contained in the acid gas absorbent is preferable to be 10 mass % to 55 mass %. In general, the absorption amount, the desorption amount of carbon dioxide per the unit capacity are larger and the absorption speed, the desorption speed of carbon dioxide are faster as the concentration of the amine component is higher, and therefore, the high concentration is preferable in an energy consumption side, a size of a plant equipment, and a process efficiency side. However, it becomes impossible for the water contained in the absorbing liquid to fully exhibit a function as an activator relative to the absorption of carbon dioxide when the concentration of the amine component in the absorbing liquid is too high. Besides, defects such as an increase of viscosity of the absorbing liquid become unable to disregard when the concentration of the amine component in the absorbing liquid is too high.

When the content of the secondary amine compound (4) is 55 mass % or less, phenomena such as the increase of the viscosity of the absorbing liquid, the deterioration of the function of water as the activator are not recognized. Besides, the content of the secondary amine compound (4) is set to be 10 mass or more, and thereby, it is possible to obtain the enough absorption amount, absorption speed of carbon dioxide, and to obtain excellent process efficiency.

Not only the absorption amount of carbon dioxide and the absorption speed of carbon dioxide are high but also the desorption amount of carbon dioxide and the desorption speed of carbon dioxide are high when the acid gas absorbent of which content of the secondary amine compound (4) is within the range of 10 mass % to 55 mass % is used for carbon dioxide recovery. Accordingly, it is advantageous in a point that the recovery of carbon dioxide can be performed effectively. The content of the secondary amine compound (4) is more preferable to be 20 mass % to 50 mass %.

It is preferable that the secondary amine compound (4) is used by mixing with the reaction accelerator composed of the alkanolamines and/or a hetero cyclic amine compound represented by the following general formula (2) (hereinafter referred to as the hetero cyclic amine compound (2)).

(2)

In the formula (2), the $R^5$ represents a hydrogen atom or a substituted or non-substituted alkyl group of which carbon number is 1 to 4. The $R^6$ represents the substituted or non-substituted alkyl group of which carbon number is 1 to 4 coupled to the carbon atom. The "n" represents an integer number of 1 to 3, the "m" represents an integer number of 1 to 4, and the "p" represents an integer number of "0" (zero) to 12. When the "n" is 2 to 3, the nitrogen atoms are not directly coupled with each other.

In the present embodiment, it is possible to mix, for example, the secondary amine compound (4) and the reaction accelerator composed of the alkanolamines and/or the hetero cyclic amine compound (2). In addition, it is possible to use the one in which the mixture of the secondary amine compound (4) and the alkanolamines and/or the hetero cyclic amine compound (2) is made to be, for example, a water solution as the acid gas absorbent.

The secondary amine compound (4) is mixed with the alkanolamines and/or the hetero cyclic amine compound (2) to be used, and thereby, it is possible to further improve the absorption amount of carbon dioxide per unit mol of the secondary amine compound (4), the absorption amount of carbon dioxide per unit volume of the acid gas absorbent and the absorption speed of carbon dioxide. Besides, the secondary amine compound (4) is mixed with the alkanolamines and/or the hetero cyclic amine compound (2) to be used, and thereby, an energy separating the acid gas after the absorption of carbon dioxide (acid gas desorption energy) is lowered, and it becomes possible to reduce the energy when the acid gas absorbent is regenerated.

As concrete examples and preferable examples of alkanolamine used as the reaction accelerator in the second embodiment, the similar ones as the concrete examples and the preferable examples cited in the first embodiment can be cited.

As concrete examples and preferable examples of the hetero cyclic amine compound (2) used as the reaction accelerator in the second embodiment, the similar ones as the concrete examples and the preferable examples cited in the first embodiment can be cited.

It is preferable that a content of the reaction accelerator (the alkanolamines and/or the hetero cyclic amine compound (2)) contained in the acid gas absorbent according to the second embodiment is 1 mass % to 20 mass %. There is a possibility that the effect improving the absorption speed of carbon dioxide cannot be fully obtained when the content of the reaction accelerator contained in the acid gas absorbent is less than 1 mass %. There is a possibility that the reactivity conversely deteriorates because the viscosity of the absorbent becomes excessively high when the content of the reaction accelerator contained in the acid gas absorbent exceeds 20 mass %. The content of the reaction accelerator (the alkanolamines and/or the hetero cyclic amine compound (2)) contained in the acid gas absorbent according to the second embodiment is more preferable to be 5 mass % to 15 mass %.

The acid gas absorbent may contain an anticorrosive of phosphoric acid based and so on to prevent a corrosion of the plant equipment, a defoamer of silicon based and so on to prevent effervescence, an antioxidant to prevent deterioration of the acid gas absorbent, and so on, in addition to the amine compound and the reaction accelerator as stated above.

An acid gas removal method according to the present embodiment is the one in which exhaust gas containing acid gas is brought into contact with an acid gas absorbent made up by dissolving the amine compound described in the above-stated embodiment in a solvent, and the acid gas is absorbed and separated to be removed from the exhaust gas containing the acid gas.

A basic constitution of an absorbing and separating process of carbon dioxide comprises: a process bringing exhaust gas containing carbon dioxide into contact with an acid gas absorbent to make the acid gas absorbent absorb carbon dioxide (carbon dioxide absorbing process); and a process heating the acid gas absorbent to which carbon dioxide is absorbed obtained at the carbon dioxide absorbing process to desorb and recover carbon dioxide (carbon dioxide separating process).

A method to bring the gas containing carbon dioxide into contact with a water solution containing the acid gas absorbent is not particularly limited, but for example, it is performed by a method in which the gas containing carbon dioxide is bubbled in the acid gas absorbent to absorb carbon dioxide, a method in which the acid gas absorbent is atomized and sprayed in a gas flow containing carbon dioxide (atomizing and spraying method), a method in which the gas containing carbon dioxide is brought into countercurrent contact with the acid gas absorbent in an absorption tower containing filler made of a porcelain or a metal net, or the like.

A temperature of the acid gas absorbent when the gas containing carbon dioxide is absorbed in the water solution is generally set within a range from a room temperature to 60° C. or less. It is preferable to be set at 50° C. or less, and more preferable to be set at approximately 20° C. to 45° C. The absorption amount of the acid gas increases as it is performed at a lower temperature, but a lower limit value of the process temperature is determined by a gas temperature and a heat recovery target and so on in the process. A pressure at the carbon dioxide absorption time is generally set at approximately the atmospheric pressure. It is possible to pressurize up to higher pressure to enhance the absorption performance, but it is preferable to set under the atmospheric pressure to suppress energy consumption required for compression.

In the carbon dioxide absorption process, the carbon dioxide absorption amount at the carbon dioxide absorption time (40° C.) of the acid gas absorbent containing the amine compound according to the above-stated embodiment for 10 mass % to 55 mass % is approximately 0.26 mol to 0.62 mol per 1 mol of amine contained in the absorbent. Besides, in the carbon dioxide absorption process, the carbon dioxide absorption speed of the acid gas absorbent containing the amine compound according to the embodiment for 10 mass % to 55 mass % after a few minutes have passed since the absorption of carbon dioxide is started is approximately 0.029 mol/L/min to 0.038 mol/L/min.

Here, a carbon dioxide saturation absorption amount is a value in which an inorganic carbon amount in the acid gas absorbent is measured by an infrared gas concentration measurement device. Besides, the carbon dioxide absorption speed is a value measured by using an infrared carbon dioxide sensor at a time when a few minutes have passed since the absorption of carbon dioxide is started.

A method desorbing carbon dioxide by heating the acid gas absorbent as same as distillation and beating in an iron pot, a method heating by extending a liquid interface in a plate tower, a spray tower, and the regeneration tower containing filler made of a porcelain or a metal net, or the like, and so on can be cited as a method separating carbon dioxide from the acid gas absorbent absorbing carbon dioxide, and recovering pure or high-concentration carbon dioxide. Carbon dioxide is thereby released and discharged from anionic carbamate and bicarbonate.

A temperature of the acid gas absorbent at the carbon dioxide separation time is normally set to be 70° C. or more, it is preferable to be 80° C. or more, and more preferable to be approximately 90° C. to 120° C. The absorption amount increases as the temperature is higher, but the energy required for the heating of the absorbing liquid increases if the temperature is increased. Accordingly, the temperature of the acid gas absorbent at the carbon dioxide separation time is determined by the gas temperature, the heat recovery target and so on in the process. The pressure at the carbon dioxide desorption time is generally set at approximately the atmospheric pressure. It is possible to decrease the pressure to a lower pressure to enhance the desorption performance, but it is preferable to be set under the atmospheric pressure to suppress energy consumption required to decrease the pressure.

The carbon dioxide desorption amount at the carbon dioxide desorption time (80° C.) of the water solution containing the amine compound according to the above-stated embodiment for 10 mass % to 55 mass % is approximately 0.15 mol to 0.47 mol per 1 mol of amine contained in the absorbent.

The acid gas absorbent after carbon dioxide is separated is transferred to the carbon dioxide absorption process again to be cyclic used (recycled). Besides, the heat generated at the carbon dioxide absorption time is generally heat exchanged by a heat exchanger for preheating the water solution injected into the regeneration tower during a recycle process of the water solution and cooled.

Purity of carbon dioxide recovered as stated above is normally extremely high such as approximately 95 vol % to 99 vol %. This pure carbon dioxide or carbon dioxide in high concentration are used as chemicals, synthetic raw materials of high polymer, a coolant for freeze foods, and so on. In addition, it is possible to isolate and store the recovered carbon dioxide to an underground or the like by means which is currently technically developed.

The process separating carbon dioxide from the acid gas absorbent and regenerating the acid gas absorbent is a part consuming the largest amount of energy among the above-stated processes, and the energy of approximately 50% to 80% within the whole process is consumed at the process. Accordingly, it is possible to reduce a cost of the absorbing and separating process of carbon dioxide and to perform the removal of the acid gas from the exhaust gas advantageously from a economy standpoint by reducing the consumption energy at the regeneration process of the acid gas absorbent. from a point of view of According to the present embodiment, it is possible to reduce the energy required for the desorption of carbon dioxide (regeneration process) by using the acid gas absorbent according to the above-stated embodiment. Accordingly, it is possible to perform the absorbing and separating process of carbon dioxide under an economically advantageous condition.

Besides, the amine compound according to the embodiment has extremely high corrosion resistance relative to a metal material such as a carbon steel compared to alkanolamines such as 2-aminoethanol which is conventionally used as the acid gas absorbent. Accordingly, it is costly advantageous by using the acid gas removal method using the acid gas absorbent as stated above because it is not necessary to use expensive anticorrosion steel in, for example, a plant construction.

An acid gas removal device according to the present embodiment comprises: an absorption tower in which gas containing acid gas is brought into contact with an acid gas absorbent according to the embodiment to remove the acid gas from the gas; and a regeneration tower removing the acid gas from the acid gas absorbent absorbing the acid gas to regenerate the acid gas absorbent reused at the absorption tower.

FIG. 1 is a schematic diagram of an acid gas removal device according to the embodiment. An acid gas removal device 1 includes: an absorption tower 2 in which gas containing acid gas (hereinafter, referred to as exhaust gas) is brought into contact with an acid gas absorbent to absorb and remove the acid gas from the exhaust gas; and a regeneration tower 3 separating the acid gas from the acid gas absorbent absorbing the acid gas to regenerate the acid gas absorbent. Hereinafter, a case when the acid gas is carbon dioxide is described as an example.

As illustrated in FIG. 1, exhaust gas containing carbon dioxide such as exhaust combustion gas discharged from a thermal power station is introduced to a lower part of the absorption tower 2 by passing through a gas supply port 4. This exhaust gas is shut in the absorption tower 2, and it is brought into contact with an acid gas absorbent supplied from an acid gas absorbent supply port 5 at an upper part of the absorption tower 2. The acid gas absorbent according to the above-stated embodiment is used as the acid gas absorbent.

A pH value of the acid gas absorbent is to be adjusted at least at 9 or more, but an optimal condition may be appropriately selected depending on a kind or a concentration of harmful gas contained in the exhaust gas, a flow rate, and so on. Besides, the other compounds such as nitrogen-containing compound improving the absorption performance of carbon dioxide, antioxidant, pH adjusting agent may be contained in the acid gas absorbent with an arbitrary rate in addition to the above-stated amine based compound, and the solvent such as water.

As stated above, the exhaust gas is brought into contact with the acid gas absorbent, and thereby, carbon dioxide within the exhaust gas is absorbed by the acid gas absorbent and removed. The exhaust gas after carbon dioxide is removed is discharged toward outside of the absorption tower 2 from a gas discharge port 6.

The acid gas absorbent absorbing carbon dioxide is transferred to a heat exchanger 7, a heater 8 to be heated, and thereafter, transferred to the regeneration tower 3. The acid gas absorbent transferred to the regeneration tower 3 is moved from an upper part to a lower part of the regeneration tower 3. Carbon dioxide within the acid gas absorbent is desorbed during the moving, and the acid gas absorbent is regenerated.

The acid gas absorbent regenerated in the regeneration tower 3 is transferred to the heat exchanger 7, an absorbing liquid cooler 10 by a pump 9, and returned to the absorption tower 2 from the acid gas absorbent supply port 5.

On the other hand, carbon dioxide separated from the acid gas absorbent is brought into contact with reflux water supplied from a reflux drum 11 at the upper part of the regeneration tower 3, and discharged toward outside of the regeneration tower 3. The reflux water in which carbon dioxide is dissolved is cooled in a reflux condenser 12, and thereafter, it is separated from liquid component in which vapor with carbon dioxide is condensed in the reflux drum 11. This liquid component is introduced to the carbon dioxide recovery process by a recovery carbon dioxide line 13. On the other hand, the reflux water from which carbon dioxide is separated is transferred to the regeneration tower 3 by a reflux water pump 14.

According to the acid gas removal device 1 of the present embodiment, it becomes possible to perform the absorption and the removal of carbon dioxide with high efficiency by using the acid gas absorbent excellent in the absorption feature and desorption feature of carbon dioxide.

Hereinabove, the embodiments of the present invention are described with reference to concrete examples, but the above-stated examples are cited just as an example of the present invention, and not to intend to limit the invention. Besides, a description relating to portions and so on which are not directly necessary for the explanation of the present invention is not given in the description of each embodiment in the acid gas absorbent, the acid gas removal device, and the acid gas removal method. However, each element required thereto may be appropriately selected to be used.

In addition, an acid gas absorbent, an acid gas removal device, and an acid gas removal method which include elements of the present invention and capable of being appropriately changed by a person skilled in the art without departing from the spirit or essential characteristics thereof are embraced therein. The range of the present invention is defined by a range of claims and a range of equivalency thereof.

Hereinafter, the embodiments are described in more detail with reference to examples, a comparative example, but the present invention is not limited to these examples.

Example 1

A water solution of 50 ml is prepared by dissolving 45 mass % of N-(sec-butyl)-N-methylaminoethanol, and 5 mass % of piperidine in water (hereinafter, referred to as absorbing liquid). This absorbing liquid is filled in a test tube, heated to be 40° C., then mixed gas containing carbon dioxide ($CO_2$) for 10 vol %, nitrogen ($N_2$) gas for 90 vol % is aerated at a flow rate of 500 mL/min. The absorption performance is evaluated by measuring the carbon dioxide ($CO_2$) concentration within the gas at an exit of the test tube by using an infrared gas concentration measurement device (manufactured by Shimadzu Corporation, name of article: "CGT-700"). A Teflon (registered trademark) tube (inside diameter; 1.59 mm, outside diameter: 3.17 mm) of ⅛ inches is set at a gas introducing port to the amine solution in the test tube. Besides, the solution after the mixed gas is absorbed at 40° C. as stated above is heated to be 80° C., 100% nitrogen ($N_2$) gas is aerated at a flow rate of 500 mL/min, and the $CO_2$ concentration in the absorbing liquid is measured by using the infrared gas concentration measurement device to evaluate a release performance.

The absorption speed of carbon dioxide of the absorbing liquid is the speed measured at a time after two minutes have passed since the absorption of carbon dioxide is started. The heat of reaction is measured by using a calorimeter "DRC Evolution" (product name, manufactured by SETRAM company).

A diffusion performance of the amine compound is evaluated as stated below. Namely, the absorbing liquid is put into a flask with a cooling tube, and thereafter, it is heated to 120° C. together with the flask. A gas component diffused from the cooling tube is collected, and an amount of the amine compound contained in the collected gas is measured.

The absorption amount of carbon dioxide of the absorbing liquid at 40° C. is 0.47 mol per 1 mol of the amine compound in the absorbing liquid. Besides, the absorption amount of carbon dioxide ($CO_2$) of the absorbing liquid at 80° C. is 0.20 mol per 1 mol of the amine compound. During a process absorbing carbon dioxide ($CO_2$) at 40° C. and desorbing carbon dioxide ($CO_2$) at 80° C., $CO_2$ of 0.27 mol per 1 mol of the amine compound is recovered. The absorption speed of carbon dioxide is 0.034 mol/L/min.

Example 2

The absorbing liquid is prepared as same as the example 1 except that 2-ethylpiperazine is used instead of piperidine. The absorption amount of carbon dioxide and the absorption speed of carbon dioxide are measured under the same conditions by using the same devices as the example 1. The absorption amount of carbon dioxide at 40° C. is 0.53 mol, and the absorption amount of carbon dioxide at 80° C. is 0.18 mol per 1 mol of the amine compound in the absorbing liquid. Carbon dioxide of 0.35 mol per 1 mol of the amine compound in the absorbing liquid is recovered. The absorption speed of carbon dioxide is 0.035 mol/L/min.

Example 3

The absorbing liquid is prepared as same as the example 1 except that piperazine is used instead of piperidine. The absorption amount of carbon dioxide and the absorption speed of carbon dioxide are measured under the same conditions by using the same devices as the example 1. The absorption amount of carbon dioxide at 40° C. is 0.58 mol, and the absorption amount of carbon dioxide at 80° C. is 0.11 mol per 1 mol of the amine compound in the absorbing liquid. Carbon dioxide of 0.47 mol per 1 mol of the amine compound in the absorbing liquid is recovered. The absorption speed of carbon dioxide is 0.037 mol/L/min.

Example 4

The absorbing liquid is prepared as same as the example 1 except that 2,5-dimethylpiperazine is used instead of piperidine. The absorption amount of carbon dioxide and the absorption speed of carbon dioxide are measured under the same conditions by using the same devices as the example 1. The absorption amount of carbon dioxide at 40° C. is 0.49 mol, and the absorption amount of carbon dioxide at 80° C. is 0.18 mol per 1 mol of the amine compound in the absorbing liquid. Carbon dioxide of 0.31 mol per 1 mol of the amine compound in the absorbing liquid is recovered. The absorption speed of carbon dioxide is 0.035 mol/L/min.

Example 5

The absorbing liquid is prepared as same as the example 1 except that N-(3-pentyl)-N-methylaminoethanol is used instead of N-(sec-butyl)-N-methylaminoethanol, and piperazine is used instead of piperidine. The absorption amount of carbon dioxide and the absorption speed of carbon dioxide are measured under the same conditions by using the same devices as the example 1. The absorption amount of carbon dioxide at 40° C. is 0.48 mol, and the absorption amount of carbon dioxide at 80° C. is 0.13 mol per 1 mol of the amine compound in the absorbing liquid. Carbon dioxide of 0.45 mol per 1 mol of the amine compound in the absorbing liquid is recovered. The absorption speed of carbon dioxide is 0.036 mol/L/min.

Example 6

The absorbing liquid is prepared as same as the example 1 except that N-(2-hexyl)-N-methylaminoethanol is used instead of N-(sec-butyl)-N-methylaminoethanol, and 2,5-dimethylpiperazine is used instead of piperidine. The absorption amount of carbon dioxide and the absorption speed of carbon dioxide are measured under the same conditions by using the same devices as the example 1. The absorption amount of carbon dioxide at 40° C. is 0.44 mol, and the absorption amount of carbon dioxide at 80° C. is 0.14 mol per 1 mol of the amine compound in the absorbing liquid. Carbon dioxide of 0.30 mol per 1 mol of the amine compound in the absorbing liquid is recovered. The absorption speed of carbon dioxide is 0.034 mol/L/min.

Example 7

The absorbing liquid is prepared as same as the example 1 except that N-(2-heptyl)-N-methylaminoethanol is used instead of N-(sec-butyl)-N-methylaminoethanol, and 2,5-dimethylpiperazine is used instead of piperidine. The absorption amount of carbon dioxide and the absorption speed of carbon dioxide are measured under the same conditions by using the same devices as the example 1. The absorption amount of carbon dioxide at 40° C. is 0.41 mol, and the absorption amount of carbon dioxide at 80° C. is 0.14 mol per 1 mol of the amine compound in the absorbing liquid. Carbon dioxide of 0.27 mol per 1 mol of the amine compound in the absorbing liquid is recovered. The absorption speed of carbon dioxide is 0.034 mol/L/min.

Example 8

The absorbing liquid is prepared as same as the example 1 except that N-cyclopentyl-N-methylaminoethanol is used instead of N-(sec-butyl)-N-methylaminoethanol, and piperazine is used instead of piperidine. The absorption amount of carbon dioxide and the absorption speed of carbon dioxide are measured under the same conditions by using the same devices as the example 1. The absorption amount of carbon dioxide at 40° C. is 0.43 mol, and the absorption amount of carbon dioxide at 80° C. is 0.04 mol per 1 mol of the amine compound in the absorbing liquid. Carbon dioxide of 0.39 mol per 1 mol of the amine compound in the absorbing liquid is recovered. The absorption speed of carbon dioxide is 0.036 mol/L/min.

Example 9

The absorbing liquid is prepared as same as the example 1 except that N-cyclohexyl-N-methylaminoethanol is used instead of N-(sec-butyl)-N-methylaminoethanol, and piperazine is used instead of piperidine. The absorption amount of carbon dioxide and the absorption speed of carbon dioxide are measured under the same conditions by using the same devices as the example 1. The absorption amount of carbon dioxide at 40° C. is 0.37 mol, and the absorption amount of carbon dioxide at 80° C. is 0.10 mol per 1 mol of the amine compound in the absorbing liquid. Carbon dioxide of 0.27 mol per 1 mol of the amine compound in the absorbing liquid is recovered. The absorption speed of carbon dioxide is 0.036 mol/L/min.

Example 10

The absorbing liquid is prepared as same as the example 1 except that N-cyclobutyl-N-methylaminoethanol is used instead of N-(sec-butyl)-N-methylaminoethanol, and piperazine is used instead of piperidine. The absorption amount of carbon dioxide and the absorption speed of carbon dioxide are measured under the same conditions by using the same devices as the example 1. The absorption amount of carbon dioxide at 40° C. is 0.39 mol, and the absorption amount of carbon dioxide at 80° C. is 0.05 mol per 1 mol of the amine compound in the absorbing liquid. Carbon dioxide of 0.34 mol per 1 mol of the amine compound in the absorbing liquid is recovered. The absorption speed of carbon dioxide is 0.036 mol/L/min.

Example 11

The absorbing liquid is prepared as same as the example 1 except that 3-(N-cyclopentyl-N-methylamino)-1-propanol is used instead of N-(sec-butyl)-N-methylaminoethanol, and piperazine is used instead of piperidine. The absorption amount of carbon dioxide and the absorption speed of carbon dioxide are measured under the same conditions by using the same devices as the example 1. The absorption amount of carbon dioxide at 40° C. is 0.38 mol, and the absorption amount of carbon dioxide at 80° C. is 0.04 mol per 1 mol of the amine compound in the absorbing liquid. Carbon dioxide of 0.34 mol per 1 mol of the amine compound in the absorbing liquid is recovered. The absorption speed of carbon dioxide is 0.035 mol/L/min.

Example 12

The absorbing liquid is prepared as same as the example 1 except that 30 mass % of N-cyclopentyl-N-methylaminoethanol is used instead of N-(sec-butyl)-N-methylaminoethanol, and piperazine is used instead of piperidine. The absorption amount of carbon dioxide and the absorption speed of carbon dioxide are measured under the same conditions by using the same devices as the example 1. The absorption amount of carbon dioxide at 40° C. is 0.39 mol, and the absorption amount of carbon dioxide at 80° C. is 0.04 mol per 1 mol of the amine compound in the absorbing liquid. Carbon dioxide of 0.35 mol per 1 mol of the amine compound in the absorbing liquid is recovered. The absorption speed of carbon dioxide is 0.035 mol/L/min.

Example 13

The absorbing liquid is prepared as same as the example 1 except that N-cyclopentyl-N-methylaminoethanol is used instead of N-(sec-butyl)-N-methylaminoethanol, and 2.5 mass % of piperazine and 2.5 mass % of 2-amino-2-methyl-1-propanol are used instead of piperidine. The absorption amount of carbon dioxide and the absorption speed of carbon dioxide are measured under the same conditions by using the same devices as the example 1. The absorption amount of carbon dioxide at 40° C. is 0.48 mol, and the absorption amount of carbon dioxide at 80° C. is 0.10 mol per 1 mol of the amine compound in the absorbing liquid. Carbon dioxide of 0.38 mol per 1 mol of the amine compound in the absorbing liquid is recovered. The absorption speed of carbon dioxide is 0.036 mol/L/min.

Example 14

The absorbing liquid is prepared as same as the example 1 except that 2-(cyclopentylamino)ethanol is used instead of N-(sec-butyl)-N-methylaminoethanol, and piperazine is used instead of piperidine. The absorption amount of carbon dioxide and the absorption speed of carbon dioxide are measured under the same conditions by using the same devices as the example 1. The absorption amount of carbon dioxide at 40° C. is 0.56 mol, and the absorption amount of carbon dioxide at 80° C. is 0.25 mol per 1 mol of the amine compound in the absorbing liquid. Carbon dioxide of 0.31 mol per 1 mol of the amine compound in the absorbing liquid is recovered. The absorption speed of carbon dioxide is 0.036 mol/L/min.

Example 15

The absorbing liquid is prepared as same as the example 1 except that 2-(2-butylamino)ethanol is used instead of N-(sec-butyl)-N-methylaminoethanol, and piperazine is used instead of piperidine. The absorption amount of carbon dioxide and the absorption speed of carbon dioxide are measured under the same conditions by using the same devices as the example 1. The absorption amount of carbon dioxide at 40° C. is 0.57 mol, and the absorption amount of carbon dioxide at 80° C. is 0.24 mol per 1 mol of the amine compound in the absorbing liquid. Carbon dioxide of 0.33 mol per 1 mol of the amine compound in the absorbing liquid is recovered. The absorption speed of carbon dioxide is 0.036 mol/L/min.

Example 16

The absorbing liquid is prepared as same as the example 1 except that 2-(2-pentylamino) ethanol is used instead of N-(sec-butyl)-N-methylaminoethanol, and piperazine is used instead of piperidine. The absorption amount of carbon dioxide and the absorption speed of carbon dioxide are measured under the same conditions by using the same devices as the example 1. The absorption amount of carbon dioxide at 40° C. is 0.55 mol, and the absorption amount of carbon dioxide at 80° C. is 0.25 mol per 1 mol of the amine compound in the absorbing liquid. Carbon dioxide of 0.30 mol per 1 mol of the amine compound in the absorbing liquid is recovered. The absorption speed of carbon dioxide is 0.036 mol/L/min.

Example 17

The absorbing liquid is prepared as same as the example 1 except that 2-(3-pentylamino) ethanol is used instead of N-(sec-butyl)-N-methylaminoethanol, and piperazine is used instead of piperidine. The absorption amount of carbon dioxide and the absorption speed of carbon dioxide are measured under the same conditions by using the same devices as the example 1. The absorption amount of carbon dioxide at 40° C. is 0.53 mol, and the absorption amount of carbon dioxide at 80° C. is 0.25 mol per 1 mol of the amine compound in the absorbing liquid. Carbon dioxide of 0.28 mol per 1 mol of the amine compound in the absorbing liquid is recovered. The absorption speed of carbon dioxide is 0.036 mol/L/min.

Example 18

The absorbing liquid is prepared as same as the example 1 except that 2-(2-hexylamino)ethanol is used instead of N-(sec-butyl)-N-methylaminoethanol, and piperazine is used instead of piperidine. The absorption amount of carbon dioxide and the absorption speed of carbon dioxide are measured under the same conditions by using the same devices as the example 1. The absorption amount of carbon dioxide at 40° C. is 0.51 mol, and the absorption amount of carbon dioxide at 80° C. is 0.26 mol per 1 mol of the amine compound in the absorbing liquid. Carbon dioxide of 0.25 mol per 1 mol of the amine compound in the absorbing liquid is recovered. The absorption speed of carbon dioxide is 0.036 mol/L/min.

Example 19

The absorbing liquid is prepared as same as the example 1 except that 2-(3-hexylamino)ethanol is used instead of N-(sec-butyl)-N-methylaminoethanol, and piperazine is used instead of piperidine. The absorption amount of carbon dioxide and the absorption speed of carbon dioxide are measured under the same conditions by using the same devices as the example 1. The absorption amount of carbon dioxide at 40° C. is 0.50 mol, and the absorption amount of carbon dioxide at 80° C. is 0.27 mol per 1 mol of the amine compound in the absorbing liquid. Carbon dioxide of 0.23 mol per 1 mol of the amine compound in the absorbing liquid is recovered. The absorption speed of carbon dioxide is 0.034 mol/L/min.

Example 20

The absorbing liquid is prepared as same as the example 1 except that 30 mass % of 2-(cyclopentylamino) ethanol is used instead of N-(sec-butyl)-N-methylaminoethanol, and piperazine is used instead of piperidine. The absorption amount of carbon dioxide and the absorption speed of carbon dioxide are measured under the same conditions by using the same devices as the example 1. The absorption amount of carbon dioxide at 40° C. is 0.56 mol, and the absorption amount of carbon dioxide at 80° C. is 0.24 mol per 1 mol of the amine compound in the absorbing liquid. Carbon dioxide of 0.32 mol per 1 mol of the amine compound in the absorbing liquid is recovered. The absorption speed of carbon dioxide is 0.037 mol/L/min.

Example 21

The absorbing liquid is prepared as same as the example 1 except that 2-(cyclobutylamino)ethanol is used instead of N-(sec-butyl)-N-methylaminoethanol, and piperazine is used instead of piperidine. The absorption amount of carbon dioxide and the absorption speed of carbon dioxide are measured under the same conditions by using the same devices as the example 1. The absorption amount of carbon dioxide at 40° C. is 0.56 mol, and the absorption amount of carbon dioxide at 80° C. is 0.25 mol per 1 mol of the amine compound in the absorbing liquid. Carbon dioxide of 0.31 mol per 1 mol of the amine compound in the absorbing liquid is recovered. The absorption speed of carbon dioxide is 0.037 mol/L/min.

Example 22

The absorbing liquid is prepared as same as the example 1 except that 2-(cyclopentylamino)-1-propanol is used instead of N-(sec-butyl)-N-methylaminoethanol. The absorption amount of carbon dioxide and the absorption speed of carbon dioxide are measured under the same conditions by using the same devices as the example 1. The absorption amount of carbon dioxide at 40° C. is 0.54 mol, and the absorption amount of carbon dioxide at 80° C. is 0.24 mol per 1 mol of the amine compound in the absorbing liquid. Carbon dioxide of 0.30 mol per 1 mol of the amine compound in the absorbing liquid is recovered. The absorption speed of carbon dioxide is 0.034 mol/L/min.

Example 23

The absorbing liquid is prepared as same as the example 1 except that 3-(cyclohexylamino)ethanol is used instead of N-(sec-butyl)-N-methylaminoethanol, and piperazine is used instead of piperidine. The absorption amount of carbon dioxide and the absorption speed of carbon dioxide are measured under the same conditions by using the same devices as the example 1. The absorption amount of carbon dioxide at 40° C. is 0.50 mol, and the absorption amount of carbon dioxide at 80° C. is 0.24 mol per 1 mol of the amine compound in the absorbing liquid. Carbon dioxide of 0.26 mol per 1 mol of the amine compound in the absorbing liquid is recovered. The absorption speed of carbon dioxide is 0.034 mol/L/min.

Example 24

The absorbing liquid is prepared as same as the example 1 except that 2-(cyclopentylamino)ethanol is used instead of N-(sec-butyl)-N-methylaminoethanol, and 2.5 mass % of piperazine, 2.5 mass % of 2-amino-2-methyl-1-propanol is used instead of piperidine. The absorption amount of carbon dioxide and the absorption speed of carbon dioxide are measured under the same conditions by using the same devices as the example 1. The absorption amount of carbon dioxide at 40° C. is 0.58 mol, and the absorption amount of carbon dioxide at 80° C. is 0.26 mol per 1 mol of the amine compound in the absorbing liquid. Carbon dioxide of 0.32 mol per 1 mol of the amine compound in the absorbing liquid is recovered. The absorption speed of carbon dioxide is 0.037 mol/L/min.

Example 25

The absorbing liquid is prepared as same as the example 1 except that 30 mass % of 2-(cyclopentylamino)ethanol is used instead of N-(sec-butyl)-N-methylaminoethanol, and piperidine is not used. The absorption amount of carbon dioxide and the absorption speed of carbon dioxide are measured under the same conditions by using the same devices as the example 1. The absorption amount of carbon dioxide at 40° C. is 0.59 mol, and the absorption amount of carbon dioxide at 80° C. is 0.25 mol per 1 mol of the amine compound in the absorbing liquid. Carbon dioxide of 0.34 mol per 1 mol of the amine compound in the absorbing liquid is recovered. The absorption speed of carbon dioxide is 0.038 mol/L/min.

Example 26

The absorbing liquid is prepared as same as the example 1 except that 30 mass % of 2-(cyclopentylamino)ethanol is used instead of N-(sec-butyl)-N-methylaminoethanol, and 5 mass % of 2-amino-2-methyl-1-propanol is used instead of piperidine. The absorption amount of carbon dioxide and the absorption speed of carbon dioxide are measured under the same conditions by using the same devices as the example 1. The absorption amount of carbon dioxide at 40° C. is 0.61 mol, and the absorption amount of carbon dioxide at 80° C. is 0.28 mol per 1 mol of the amine compound in the absorbing liquid. Carbon dioxide of 0.33 mol per 1 mol of the amine compound in the absorbing liquid is recovered. The absorption speed of carbon dioxide is 0.038 mol/L/min.

Comparative Example 1

A water solution of 50 ml is prepared by dissolving 60 mass % of n-butyldiethanolamine and 5 mass % of piperazine in water (hereinafter, referred to as absorbing liquid). After that, the absorption amount of carbon dioxide and the absorption speed of carbon dioxide are measured under the same conditions as the example 1 by using the same devices as the example 1. The absorption amount of carbon dioxide at 40° C. is 0.20 mol, and the absorption amount of carbon dioxide at 80° C. is 0.08 mol per 1 mol of the amine compound in the absorbing liquid. Carbon dioxide of 0.12 mol per 1 mol of the amine compound in the absorbing liquid is recovered. The absorption speed of carbon dioxide is 0.023 mol/L/min.

The measurement results of the absorption amount of carbon dioxide at 40° C., the absorption amount of carbon dioxide at 80° C., the recovery amount of carbon dioxide, the absorption speed of carbon dioxide, and the heat of reaction as for the examples 1 to 26, and the comparative example 1 are represented at Tables 1 to 2 together with the content of the amine compound and the reaction accelerator in the absorbing liquid. Note that in Tables 1 to 2, the absorption amount of carbon dioxide and the recovery amount of carbon dioxide are the ones representing the absorption amount and the recovery amount per 1 mol of the amine compound contained in the absorbing liquid by the number of moles.

TABLE 1

| | AMINE COMPOUND [MASS %] | reaction accelerator AMINE COMPOUND [MASS %] | reaction accelerator HETERO CYCLIC AMINE COMPOUND [MASS %] | $CO_2$ ABSORPTION AMOUNT (40° C.) [mol] | $CO_2$ ABSORPTION AMOUNT (80° C.) [mol] | $CO_2$ RECOVERY AMOUNT [mol] | $CO_2$ ABSORPTION SPEED [mol/L/min] | HEAT OF REACTION [kJ/mol] |
|---|---|---|---|---|---|---|---|---|
| EXAMPLE 1 | 45 | | 5 | 0.47 | 0.20 | 0.27 | 0.034 | 67 |
| EXAMPLE 2 | 45 | | 5 | 0.53 | 0.18 | 0.35 | 0.035 | 67 |
| EXAMPLE 3 | 45 | | 5 | 0.58 | 0.11 | 0.47 | 0.037 | 66 |
| EXAMPLE 4 | 45 | | 5 | 0.49 | 0.18 | 0.31 | 0.035 | 67 |
| EXAMPLE 5 | 45 | | 5 | 0.48 | 0.13 | 0.45 | 0.036 | 67 |
| EXAMPLE 6 | 45 | | 5 | 0.44 | 0.14 | 0.30 | 0.034 | 67 |
| EXAMPLE 7 | 45 | | 5 | 0.41 | 0.14 | 0.27 | 0.034 | 67 |
| EXAMPLE 8 | 45 | | 5 | 0.43 | 0.04 | 0.39 | 0.036 | 66 |
| EXAMPLE 9 | 45 | | 5 | 0.37 | 0.10 | 0.27 | 0.036 | 66 |
| EXAMPLE 10 | 45 | | 5 | 0.39 | 0.05 | 0.34 | 0.036 | 66 |
| EXAMPLE 11 | 45 | | 5 | 0.38 | 0.04 | 0.34 | 0.035 | 66 |
| EXAMPLE 12 | 30 | | 5 | 0.39 | 0.04 | 0.35 | 0.035 | 66 |
| EXAMPLE 13 | 45 | 2.5 | 2.5 | 0.48 | 0.10 | 0.38 | 0.036 | 71 |

TABLE 2

| | AMINE COMPOUND [MASS %] | reaction accelerator AMINE COMPOUND [MASS %] | reaction accelerator HETERO CYCLIC AMINE COMPOUND [MASS %] | $CO_2$ ABSORPTION AMOUNT (40° C.) [mol] | $CO_2$ ABSORPTION AMOUNT (80° C.) [mol] | $CO_2$ RECOVERY AMOUNT [mol] | $CO_2$ ABSORPTION SPEED [mol/L/min] | HEAT OF REACTION [kJ/mol] |
|---|---|---|---|---|---|---|---|---|
| EXAMPLE 14 | 45 | | 5 | 0.56 | 0.25 | 0.31 | 0.036 | 74 |
| EXAMPLE 15 | 45 | | 5 | 0.57 | 0.24 | 0.33 | 0.036 | 75 |
| EXAMPLE 16 | 45 | | 5 | 0.55 | 0.25 | 0.30 | 0.036 | 75 |
| EXAMPLE 17 | 45 | | 5 | 0.53 | 0.25 | 0.28 | 0.036 | 75 |
| EXAMPLE 18 | 45 | | 5 | 0.51 | 0.26 | 0.25 | 0.036 | 75 |
| EXAMPLE 19 | 45 | | 5 | 0.50 | 0.27 | 0.23 | 0.034 | 75 |
| EXAMPLE 20 | 30 | | 5 | 0.56 | 0.24 | 0.32 | 0.037 | 74 |

TABLE 2-continued

|  | reaction accelerator | | | | | | | |
|---|---|---|---|---|---|---|---|---|
|  | AMINE COMPOUND [MASS %] | AMINE COMPOUND [MASS %] | HETERO CYCLIC AMINE COMPOUND [MASS %] | $CO_2$ ABSORPTION AMOUNT (40° C.) [mol] | $CO_2$ ABSORPTION AMOUNT (80° C.) [mol] | $CO_2$ RECOVERY AMOUNT [mol] | $CO_2$ ABSORPTION SPEED [mol/L/min] | HEAT OF REACTION [kJ/mol] |
| EXAMPLE 21 | 45 |  | 5 | 0.56 | 0.25 | 0.31 | 0.037 | 75 |
| EXAMPLE 22 | 45 |  | 5 | 0.54 | 0.24 | 0.30 | 0.034 | 75 |
| EXAMPLE 23 | 45 |  | 5 | 0.50 | 0.24 | 0.26 | 0.034 | 75 |
| EXAMPLE 24 | 45 | 2.5 | 2.5 | 0.58 | 0.26 | 0.32 | 0.037 | 74 |
| EXAMPLE 25 | 30 |  |  | 0.59 | 0.25 | 0.34 | 0.038 | 76 |
| EXAMPLE 26 | 30 | 5 |  | 0.61 | 0.28 | 0.33 | 0.038 | 76 |
| COMPARATIVE EXAMPLE 1 | 60 |  | 5 | 0.20 | 0.08 | 0.12 | 0.023 | 66 |

As it is obvious from Tables 1 to 2, in the absorbing liquid of the examples 1 to 13 using the tertiary amine compound having the branched alkyl group or the cyclic alkyl group, the recovery amount of carbon dioxide is high, the heat of reaction is suppressed to be low, the absorption speed of carbon dioxide is high, and the absorption performance of carbon dioxide is excellent. In particular, in each of the examples 8 to 13 using the tertiary amine compound having the cyclic alkyl group, the heat of reaction is generally 66 kJ/mol, and the heat of reaction is lower compared to the examples 1 to 7 using the tertiary amine compound having the branched alkyl group. Besides, in the evaluation test of the diffusion performance, the amine compound of approximately 1 mass % is recovered in each of the examples 1 to 7 using the tertiary amine compound having the branched alkyl group, but the amine compound is seldom recovered in each of the examples 8 to 13 using the tertiary amine compound having the cyclic alkyl group. It is recognized from the above that the tertiary amine compound having the cyclic alkyl group has low diffusion performance, and the volatile thereof is suppressed. Further, in each of the examples 8 to 13, it is recognized that the recovery amount of carbon dioxide and the recovery speed of carbon dioxide equivalent to the examples 1 to 7 can be obtained.

On the other hand, in the comparative example 1 using the amine compound which does not have the branched alkyl group or the cyclic alkyl group, it is recognized that the recovery amount of carbon dioxide is low such as 0.12 mol, and the absorption speed of carbon dioxide is small.

Besides, as it is obvious from Tables 1 to 2 in the absorbing liquid of each of the examples 14 to 26 using the secondary amine compound having the branched alkyl group or the cyclic alkyl group, the absorption amount of carbon dioxide, the recovery amount of carbon dioxide are high. Besides, in each of the examples 14 to 26, the absorption speed of carbon dioxide is also high, and the absorption performance of carbon dioxide is excellent. In particular, in each of the examples 14, 20, 24 using the secondary amine compound having the cyclic alkyl group, it is recognized that the heat of reaction is lower compared to each of the examples 15 to 19 using the secondary amine compound having the branched alkyl group. Besides, in the evaluation test of the diffusion performance, the amine compound of approximately 1 mass % is recovered in each of the examples 15 to 19 using the secondary amine compound having the branched alkyl group, but the amine compound is seldom recovered in each of the example 14 and examples 20 to 26 using the secondary amine compound having the cyclic alkyl group. It is recognized from the above that the secondary amine compound having the cyclic alkyl group has low diffusion performance, and the volatile thereof is suppressed. Further, in each of the example 14 and examples 20 to 26, it is recognized that the recovery amount of carbon dioxide, the recovery speed of carbon dioxide can be obtained equivalent to the examples 15 to 19.

On the other hand, in the comparative example 1 using the amine compound which does not have the branched alkyl group or the cyclic alkyl group, it is recognized that the recovery amount of carbon dioxide is low such as 0.12 mol, and the absorption speed of carbon dioxide is also small.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An acid gas absorbent comprising at least one type of tertiary amine compound represented by the following general formula (1):

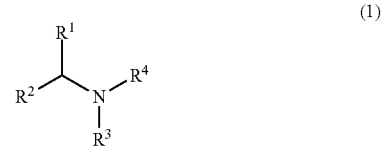

(1)

wherein
the $R^3$ represents a methyl group or an ethyl group, and the $R^4$ represents a hydroxyalkyl group;
$R^1$, $R^2$ are coupled to form a cyclopentyl group; and
wherein a content of the tertiary amine compound represented by the general formula (1) is 10 mass % to 55 mass %.

2. The acid gas absorbent according to claim 1, wherein the $R^4$ is a 2-hydroxyethyl group in the tertiary amine compound represented by the general formula (1).

3. The acid gas absorbent according to claim 1, further comprising
a reaction accelerator consisting of alkanolamines and/or a hetero cyclic amine compound represented by the following general formula (2), wherein a content of the reaction accelerator is 1 mass % to 20 mass %:

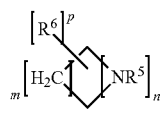
(2)

wherein the $R^5$ represents a hydrogen atom or a substituted or non-substituted alkyl group having a carbon number from 1 to 4, the $R^6$ represents a substituted or non-substituted alkyl group having a carbon number from 1 to 4 coupled to a carbon atom;

the "n" represents an integer from 1 to 3, the "m" represents an integer from 1 to 4, and the "p" represents an integer from "0" (zero) to 12;

when the "n" is 2 to 3, the nitrogen atoms are not directly coupled with each other.

4. The acid gas absorbent according to claim 3, wherein the alkanolamines are at least one type selected from a group consisting of 2-(isopropylamino)ethanol, 2-(ethylamino)ethanol, and 2-amino-2-methyl-1-propanol.

5. The acid gas absorbent according to claim 3, wherein the hetero cyclic amine compound includes at least one type selected from a group of piperazines.

6. The acid gas absorbent according to claim 5, wherein the piperazines are at least one type selected from a group consisting of piperazine, 2-methylpiperazine, 2,5-dimethylpiperazine, and 2,6-dimethylpiperazine.

7. An acid gas absorbent comprising at least one type of secondary amine compound represented by the following general formula (4):

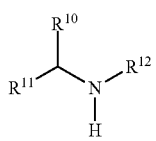
(4)

wherein the $R^{12}$ represents a hydroxyalkyl group;

the $R^{10}$, $R^{11}$ are coupled to form a cyclopentyl group;

wherein a content of the secondary amine compound represented by the general formula (4) is 10 mass % to 55 mass %.

8. The acid gas absorbent according to claim 7, wherein the $R^{12}$ is a 2-hydroxyethyl group in the secondary amine compound represented by the general formula (4).

9. The acid gas absorbent according to claim 7, further comprising a reaction accelerator consisting of alkanolamines and/or a hetero cyclic amine compound represented by the following general formula (2), wherein a content of the reaction accelerator is 1 mass % to 20 mass %:

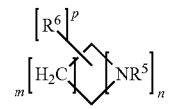
(2)

wherein the $R^5$ represents a hydrogen atom or a substituted or non-substituted alkyl group having a carbon number from 1 to 4, the $R^6$ represents a substituted or non-substituted alkyl group having a carbon number from 1 to 4 coupled to a carbon atom;

the "n" represents an integer from 1 to 3, and the "m" represents an integer from 1 to 4, and the "p" represents an integer from "0" (zero) to 12;

when the "n" is 2 to 3, the nitrogen atoms are not directly coupled with each other.

10. The acid gas absorbent according to claim 9, wherein the alkanolamines are at least one type selected from a group consisting of 2-(isopropylamino)ethanol, 2-(ethylamino)ethanol, and 2-amino-2-methyl-1-propanol.

11. The acid gas absorbent according to claim 9, wherein the hetero cyclic amine compound includes at least one type selected from a group of piperazines.

12. The acid gas absorbent according to claim 11, wherein the piperazines are at least one type selected from a group consisting of piperazine, 2-methylpiperazine, 2,5-dimethylpiperazine, and 2,6-dimethylpiperazine.

13. An acid gas removal method, comprising:
bringing gas containing acid gas into contact with the acid gas absorbent according to claim 1 to remove the acid gas from the gas containing the acid gas.

14. An acid gas removal method, comprising:
bringing gas containing acid gas into contact with the acid gas absorbent according to claim 3 to remove the acid gas from the gas containing the acid gas.

15. An acid gas removal method, comprising:
bringing gas containing acid gas into contact with the acid gas absorbent according to claim 7 to remove the acid gas from the gas containing the acid gas.

16. An acid gas removal method, comprising:
bringing gas containing acid gas into contact with the acid gas absorbent according to claim 9 to remove the acid gas from the gas containing the acid gas.

17. An acid gas removal device removing acid gas from gas containing the acid gas, comprising:
an absorption tower bringing the gas containing the acid gas into contact with the acid gas absorbent according to claim 1 to remove the acid gas from the gas; and
a regeneration tower removing the acid gas from the acid gas absorbent absorbing the acid gas and regenerating the acid gas absorbent to be reused at the absorption tower.

18. An acid gas removal device removing acid gas from gas containing the acid gas, comprising:
an absorption tower bringing the gas containing the acid gas into contact with the acid gas absorbent according to claim 3 to remove the acid gas from the gas; and
a regeneration tower removing the acid gas from the acid gas absorbent absorbing the acid gas and regenerating the acid gas absorbent to be reused at the absorption tower.

19. An acid gas removal device removing acid gas from gas containing the acid gas, comprising:

an absorption tower bringing the gas containing the acid gas into contact with the acid gas absorbent according to claim 7 to remove the acid gas from the gas; and a regeneration tower removing the acid gas from the acid gas absorbent absorbing the acid gas and regenerating the acid gas absorbent to be reused at the absorption tower.

20. An acid gas removal device removing acid gas from gas containing the acid gas, comprising:

an absorption tower bringing the gas containing the acid gas into contact with the acid gas absorbent according to claim 9 to remove the acid gas from the gas; and a regeneration tower removing the acid gas from the acid gas absorbent absorbing the acid gas and regenerating the acid gas absorbent to be reused at the absorption tower.

* * * * *